United States Patent [19]

Bourque et al.

[11] Patent Number: 5,354,854
[45] Date of Patent: Oct. 11, 1994

[54] EXPRESSION SYSTEM FOR USE IN PLANTS TO SUPPRESS FOREIGN EXPRESSION AND METHOD

[75] Inventors: June E. Bourque; William R. Folk, both of Columbia, Mo.

[73] Assignee: The Curators of the University of Missouri, Columbia, Mo.

[21] Appl. No.: 790,199

[22] Filed: Nov. 7, 1991

[51] Int. Cl.$^5$ ...................... C07H 21/02; C07H 21/04
[52] U.S. Cl. .................... 536/23.1; 536/24.1
[58] Field of Search ........................ 435/6, 91, 320.1; 536/26, 27, 28, 29, 23.1, 24.1, 22.1

[56] References Cited

PUBLICATIONS

Sheehy et al., PNAS. USA 85:8805-8809 (Dec. 1988).
Sullenger et al., Mol. Cell. Biol. 10(12):6512-6523 (Dec. 1990).
Sherwood, J. L. et al., Virology 119:150-158 (1982) "Spec. Involvement of Coat Protein in Tobacco Mosaic Virus Cross Protection".
Houba-Herin, N. et al., Nucleic Acids and Molecular Biology 1:210-220 (1987) "Antisense RNA".
Kim, S. K. et al., Cell 42:129-138 (Aug. 1985) "Stable Reduction of Thymidine Kinase Activity in Cells Exp. High Levels of Anti-Sense RNA".
Melton, D. A., Proc. Natl. Acad. Sci. USA 82:144-148 (Jan. 1985) "Injected anti-sense RNAs spec. block messenger RNA translation in vivo".
Green, P. J. et al., Ann. Rev. Biochem. 55:569-597 (1986) "Role of Antisense RNA in Gene Regulation".
van der Krol, A. R. et al, Antisense Nuc. Acids & Proteins, pp. 125-141 (1991) "Modulation of Floral Pigmentation by Antisense Technology".
Abel, P. P. et al., Proc. Natl. Acad. Sci. USA 86:6949-6952 (1989) "Delay of Disease Dev. in Transgenic Plants Exp. Tobacco Mosaic . . . ".
Ecker, J. R. et al., Proc. Natl. Acad. Sci. USA 83:5372-5376 (Aug. 1986) "Inhibition of gene exp. in plant cells by exp. of antisense RNA".
Hemenway, C. et al., EMBO J. 7:1273-1280 (1988) "Analysis of mech. of protection in transgenic plants exp. potato virus X coat protein . . .".
Rodermel, S. et al., Cell 55:673-681 (1988) "Nuclear-Organelle Interactions: Nuclear Antisense Gene Inhibits Ribulose Bisph Carboxylase . . . ".
Rothstein, S. J. et al., Proc. Natl. Acad. Sci. 84:8439-8443 (1987) "Stable & heritable inhibition of exp. of nopaline synthase in . . . ".
Hamilton, A. J. et al, Nature (London) 346:284-287 (1990) "Antisense gene that inhibits synthesis of hormone ethylene in transgenic plants".
Stockhaus, J. et al., EMBO J. 9:3013-3021 (1990) "Anti--sense RNA eff. inhibits form. of 10 kd polypep. of photosystem II in trans. potato . . . ".
Takayama, K. M. et al., CRC Crit. Rev. Biochem. & Mol. Biol. 25:155-184 (1990) "Antisense RNA".
Sharp, S. J. et al., CRC Crit. Rev. in Biochem. 19:107-144 (1985) "Structure and Transcription of Eukaryotic tRNA Genes".
Santos, T. et al., Cell 23:699-709 (1981) "Comparative Analysis of Human Chrom. Seg. Bearing Nonallelic Dispersed tRNA$_i^{met}$ Genes".
Jennings, P. A., EMBO J. 6:3043-3047 (1987) "Inhibition of SV40 relicon func. by eng. antisense RNA trans. by RNA polymerse III".
Sullenger, B. A. et al., Cell 63:601-608 (1990) "Overex. of TAR Seq. Renders Cells Resistant to Human Immunodeficiency Virus Replication".
Palmer, J. M. et al., Plant Mol. Biol 8:47-51 (1987) "Isolation and seq. analysis of nuclear tRNA$^{met-i}$ gene from sobyean".

(List continued on next page.)

Primary Examiner—Stephanie W. Zitomer
Attorney, Agent, or Firm—Reising, Ethington, Barnard, Perry & Milton

[57] ABSTRACT

An expression system and method for using the same in plants to suppress gene expression, the system including a constitutive promoter element from a tRNA gene and an antisense strand DNA fused to the promoter element for being co-transcribed with the promoter element by an RNA polymerase III to suppress expression of a gene.

2 Claims, 4 Drawing Sheets

PUBLICATIONS

Luckow, B. et al., *Nucleic Acids Res.* 15:5490 (1987) "CAT const. with mult. unique restr. sites for funct. anal. of eukaryotic promoters...".

Töpfer, R. et al., *Plant Cell Rep.* 7:225–228 (1988) "Trans. gene exp. in tobacco protoplasts: II. Compar. of reporter gene sys. for CAT...".

Takamatsu, N. et al, *EMBO J.* 6:307–311 (1987) "Expression of bacterial chloramphenicol acetyltranserase gene in tabacco plant med. by TMV-RNA".

Ebert, P. R. et al., *Proc. Natl. Acad. Sci. USA* 84:5745–5749 (1987) "Ident. of essent. upstream elem. in nopaline synthase promoter...".

Yoshinaga, S. et al. *EMBO J.* 5:343–354 (1986) "Adenovirus stim. of trans. by RNA polymerase III: evid. for E1A-dep. incr. in trans...".

Harland, R. et al., *J. Cell. Biol.* 101:1094–1099 (1985) "Trans. of mRNA injected into Xenopus Oocytes Spec. Inhibited by Antisense RNA".

Rebagliati, M. R. et al., *Cell* 48:599–605 (1987) "Antisense RNA Inj. in Fertilized Eggs reveal RNA Duplex Unwinding Activity".

Bass, B. L. et al., *Cell* 48:607–613 (1987) "Developmentally Regulated Activity That Unwinds RNA Duplexes".

Prols, M. et al., *Plant Cell Rep.* 7:221–224 (1988) "Transient gene expr. in tobacco protoplasts: I. Time course of CAT appearance".

Bogenhagen, D. F. et al., *Cell* 24:261–270 (1981) "Nucleotide Seq. in Xenopus 5S DNA Required for Transcription Termination".

Delauney, A. J. et al., *Proc. Natl. Acad. Sci. USA* 85:4300–4304 (1988) "Stable bifun. antisense trans. inhib. gene exp. in transgenic plants".

Inouye, M., *Gene* 72:25–34 (1988) "Antisense RNA: its functions and applications in gene regulation—a review".

Chang, L. J. et al., *Mol. Cell Biol.* 5:2341–2348 (1985) "Gene Exp. from Both Intronless & Intron-Cont. Rous Sarcoma Virus Clones...".

van der Krol, A. R. et al., *Gene* 72:45–50 (1988) "Antisense genes in plants: an overview".

Smith, C. C. et al., *Proc. Natl. Acad. Sci. USA* 83:2787–2791 (1986) "Antiviral effect of oligo(nucleoside methylphosphonate)...".

Zamecnik, P. C. et al., *Proc. Natl. Aca. Sci. USA* 83:4143–4146 (Jun. 1986) "Inhibition of repl. & expr. of human T-cell lymphotropic virus...".

Sandler, S. J. et al., *Plant Mol. Biol.* 11:301–310 (1988) "Inhibition of gene exp. in transformed plants by antisense RNA".

Benfey, P. N. et al., *EMBO J.* 9:1677–1696 (1990) "Tissue-spec. expr. frm CaMV 35S enhancer subdomains in early stages of plant dev.".

van der Krol, A. R. et al., *Nature* (London) 333:866–869 (1988) "Anti-sense chalcone synthase gene in trans. plants inhibits flow. pigment."

Jefferson, R. A. et al., *EMBO J.* 6:3901–3907 (1987) "GUS fusions: β-glucuronidase as sens. versatile gene fusion marker in higher plants".

Mascarenhas, J. P., *Cell. Biochem.* 15A:32 (abstract) (1991) "Male Gametophyte Expressed Genes".

Cuozzo, M., et al., *Bio/Technology* 6:549–557 (1988) "Viral Protection in Transgenic Tobacco Plants Expressing the Cumumber Mosaic...".

Smith, C., et al., *Nature* (London) 334:722–726 (1988) "Antisense RNA inhibition of polygalacturonase gene exp. in transgenic tomatoes".

EXPRESSION SYSTEM FOR USE IN PLANTS TO SUPPRESS FOREIGN EXPRESSION AND METHOD

FIELD OF THE INVENTION

This invention relates to a novel expression system and method of using the same in plants to suppress gene expression.

BACKGROUND OF THE INVENTION

Antisense RNAs are small diffusible transcripts which lack coding capacity and bind to complementary regions of a target RNA causing suppression of gene expression (2). It has been suggested that inhibition of expression occurs by RNA duplex formation (2) which in turn inhibits transport from the nucleus to cytoplasm (3) or prevents translation (4). Antisense RNAs were initially recognized in bacteria as a naturally occurring mechanism for regulation of gene expression (5). This later led to the design of artificial antisense control strategies and recently, this technology has been used for the regulation of gene expression in plants.

Plants were the first multicellular organisms in which antisense transcripts have been experimentally applied to suppress expression of endogenous genes (6). All reported antisense gene regulation in plants known to the inventors, have made use of RNAs transcribed by RNA polymerase II, particularly from the strong cauliflower mosaic virus (CaMV) 35S RNA promoter (6–15). Success has varied dependent upon the target gene and the context in which expression is studied. The inability to express sufficient levels of antisense RNAs frequently has led to incomplete and ineffective gene regulation. Alternate polymerase II promoters have been employed by some investigators seeking to improve the effectiveness of gene suppression.

An alternative approach for expressing high levels of RNA transcripts is the use of RNA polymerase III transcription units. RNA polymerase III is found in all cells where it synthesizes abundant transcripts (16). The tRNA methionine initiator ($tRNA^{met}_i$) gene encodes the initiator tRNA utilized for virtually all cytoplasmic protein synthesis in plants and consequently is expressed in every plant tissue (17). In mammalian cells, $tRNA^{met}_i$ species represents 5% of all tRNAs and it is estimated that the number of transcripts expressed from one of the genes is equal to approximately 25% of the total polyadenylated RNA present in the cell (18). The $tRNA^{met}_i$ gene is therefore very active making it well suited for antisense expression.

Antisense RNAs were first engineered to be synthesized by RNA polymerase III with co-transcription by the adenovirus VA1 gene (19). Expression of this gene linked to SV40 virus antisense sequences in monkey cells resulted in transient inhibition of SV40-replicon function by greater than 50% and demonstrated that RNA polymerase III can effectively express RNA. More recently, it has been shown that the human $tRNA^{met}_i$ gene fused to antisense templates, when introduced into animal cells, was capable of inhibiting replication of Moloney murine leukemia virus (MoMLV) by 97% and replication of HIV-1 virus by 99% (20,21).

There is no predictability between the function of antisense messages in animal studies, especially studies in cell lines, to their function in plant cells.

Animals and plant tissues undergo many different forms of development during their respective life cycles. Therefore, protein synthesis in each will be regulated according to that species. In addition, plant cells are totipotent, a single cell can regenerate into a whole plant. This is not the case with animal cells in culture. Therefore data derived from animal tissue culture systems cannot be extrapolated to include the functions of antisense messages in plant protoplast systems.

It is also not clear at what stage in protein synthesis that antisense action occurs. The antisense complementary strand may work on primary transcript (mRNA precursor) or either on the processing and/or the transport of the message from the nucleus into the cytoplasm. In transformed animal cells, interaction have been noted precisely in the nucleus where RNA:RNA hybrids formed between the mRNA and the complementary antisense RNA (3). These hybrids have never been found in plant systems.

Applicant has developed an expression system for antisense RNAs having particular use in plant biology. It utilizes a constitutive promoter element which is expressed in all plant tissues and should therefore be capable of inactivating a wide variety of gene functions.

SUMMARY OF THE INVENTION

In accordance with the present invention there is provided an expression system for use in plants to suppress gene expression, the system including a constitutive promoter element from a $tPaA^{met}_i$ gene. An antisense strand DNA is fused to the promoter element for being co-transcribed with the promoter element by RNA polymerase III to regulate expression of a gene. The present invention further provides a method of inhibiting foreign gene expression in plant cells by transcribing antisense DNA sequences fused to a constitutive promoter element from a $tRNA^{met}_i$ gene to inhibit foreign gene expression in plant cells.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
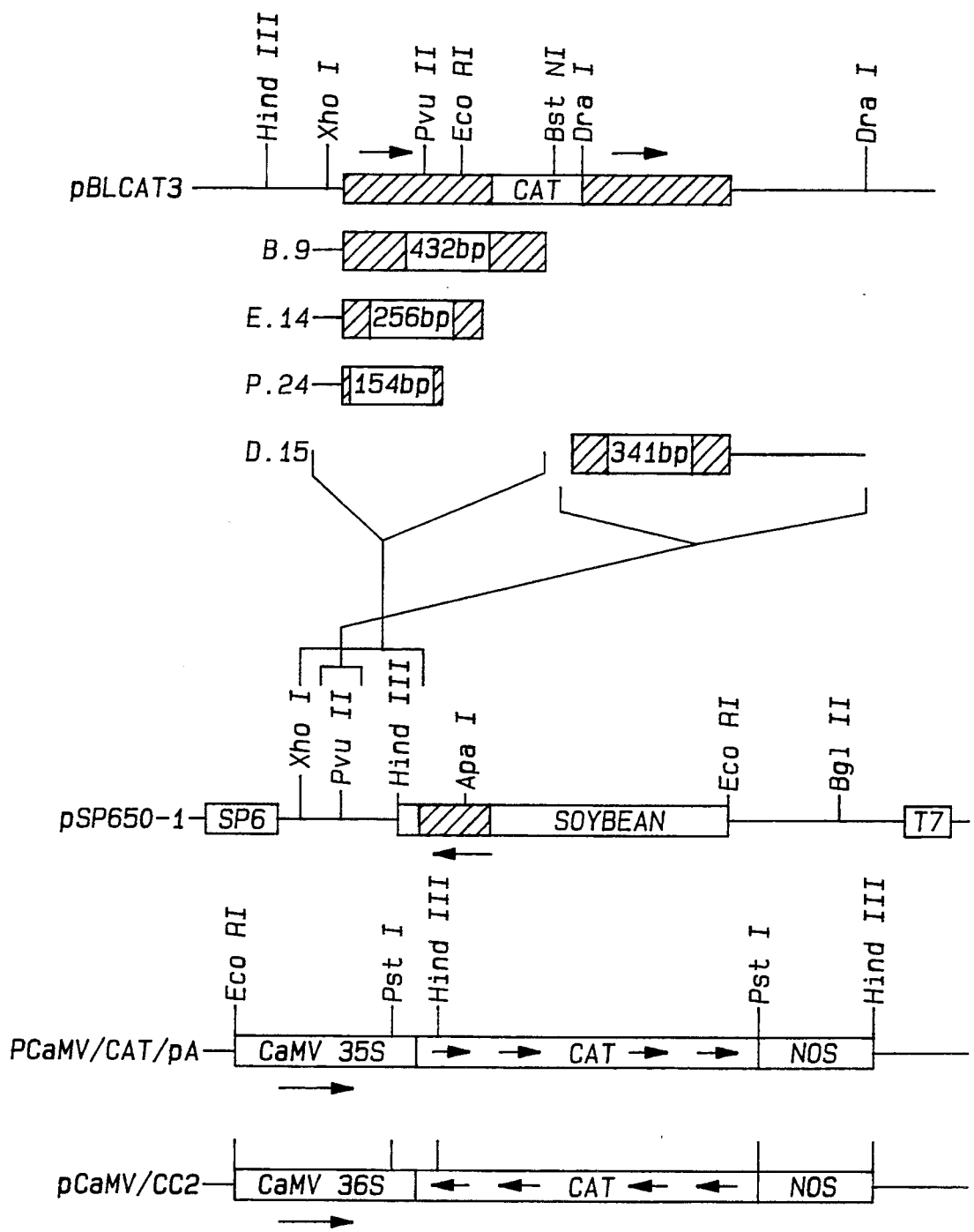
FIG. 1 shows the construction of antisense chloramphicol acetyltransferase (CAT) clones.

The present invention provides an expression system for use in plants to regulate gene expression. The experimental data set forth below indicates the ability of the present invention to be used with carrot protoplasts representative of protoplasts of the entire plant kingdom. Other researchers have shown antisense systems to function in transgenic tobacco, tomato and petunia (6–15).

Regulation of endogenous genes in plants would have a major impact on the economic value of many agronomic and horticultural crops. In a classic study, Joseph Mol and coworkers (6) have shown the use of antisense technology to alter flower pigmentation in petunia. More recently, many reports are surfacing where antisense mechanisms are being tested to regulate ethylene forming enzymes, cell wall hydrolases such as polygalacturonases and cellulases in fruit ripening, particularly in tomatoes (13,14). Some plants also express many secondary compounds as a response to some environmental stress stimulus. These compounds which constitute many important pharmaceutical agents, accumulate in low quantities due to regulatory elements in their biosynthetic pathways. Antisense strategies may be developed where pathways can be turned "on" continuously contributing to large accumulations of such products. This would not only lower the cost of pharmaceuticals in short supply but would readily make medicines more available. In addition, rare species known to produce such precious products where cultivation has not been practical would no longer be in jeopardy of extinction. The protoplast system, in itself, used in this study may also, in addition, contribute to somaclonal variation within the present cell population to produce plants with such desirable traits.

Foreign gene expression relates to the expression of nongenomic genetic material within a plant cell. This could be in the form of a virus, such as the tobacco mosaic virus or various other viruses, or other foreign genes transiently introduced into plant cells.

Antisense strategies have been employed to produce plants that are resistant to viruses (7,9,10,12), but have met with limited success. Most of these showed a delay in symptom development and did not give complete or total resistance. It is worth noting that all of these studies were done using RNA polymerase II promoter systems.

The present invention is applicable to the plant kingdom for use in suppression of such foreign genes. Hence, the present invention should find great utility in the control of plant diseases by the use of antisense genes.

The expression system of the present invention generally includes a constitutive promoter element from a tRNA gene. An antisense strand DNA is fused to the promoter element for being co-transcribed with the promoter element by RNA polymerase III to regulate expression of a gene. That is, the expression system is capable of generating antisense strand RNAs which inhibit viral gene function.

Applicant has isolated, cloned, and sequenced the soybean tRNA$^{met}_i$ genes Immediately down stream of the coding region are several unique restriction sites, in the pSP72 vector, which permits the fusion of these genes to virtually any other DNA sequence. Further, the tRNA$^{met}_i$ gene cloned into pSP72 lacks a terminator such that the tRNA$^{met}_i$ gene and a DNA sequence in reverse orientation fused thereto can be co-transcribed with the promoter element by the RNA polymerase III.

The use of RNA polymerase III transcription unit to constitutively express antisense transcripts represents a novel approach to gene regulation in plants. Chimeric tRNA genes have been shown to be highly effective in rendering mammalian cells resistant to viral replication (19,20,21). Applicant herein shows that an antisense construct containing the 3' noncoding region of the CAT gene co-transcribed with the soybean tRNA$^{met}_i$ is extremely effective in suppressing CAT activity in carrot cells.

The transcripts produced by the RNA III transcribed antisense genes are neither capped nor polyadenylated. Since the genes themselves are very small, the products are substantially shorter than those transcribed by polymerase II genes. These smaller RNA transcripts can impart an advantage both in accessibility and hybridization to target sequences (19). The tRNA structure attached to the end of the antisense sequence may also add to the stability and cellular localization which in turn influences the effectiveness as a regulator of gene function (19,36).

Each biological system may vary in susceptibility to antisense RNA (31,33). Some reports have shown that antisense RNA directed against the 5' leader and the 3' trailer of mRNAs to be particularly effective (4,36) while others report that antisense oligonucleotides complementary to splices junctions inhibit expression (38). In general, antisense directed against the 5' end of a messenger appears to the most efficient at suppressing gene expression in prokaryotic systems. In eukaryotic systems, such as reported herein, it appears that the 3' gene region can be more effective than the 5' portion of gene. It has also been reported that the most effective NOS antisense sequences in transgenic tobacco plants were derived from 3' half of the NOS gene transcript (11).

The tRNA$^{met}_i$ gene derived from soybean comprising 72 base pairs. Examples of the expression system including the constitutive promoter element and an antisense strand RNA fused to the promoter element includes 393, 497, 672 and 581 base pairs from clones pGm/P.24, pGm/E.14, pGm/B.9 and pGM/D.15 respectively. Nos. 1–4.

The present invention further provides a method of specifically suppressing gene expression in plant cells, generally including the steps of transcribing antisense RNA sequences fused to a constitutive promoter element from a tRNA gene. More specifically, the antisense RNA sequence is fused to the tRNA$^{met}_i$ gene. In general terms, the fusing step is accomplished by cloning the promoter element of the tRNA$^{met}_i$ gene to a portion of the gene to be used as the antisense template which is transcribed together by RNA polymerase III in the plant cells. More specific methods of cloning are described in the experimental section.

EXPERIMENTATION

Plasmid Construction

Antisense sequences constructed from the 5' portion of the CAT gene were generated by endonuclease cleavage at the XhoI site in the polylinker region of pBLCAT3 (23) which linearized the DNA 39 bp upstream of the ATG translation start site.

The restriction enzyme XhoI (using standard methods common to the molecular biology field, as specified by commercial suppliers of these enzymes) was used to linearize the pBLCAT3 plasmid at the cleavage site of C/TCGAG which is located on the plasmid 39 base pairs upstream of the coding sequence for the CAT gene. This was subdivided into three (3) aliquots. The first was further digested with the restriction enzyme PvuII which cleaves at the site CAG/GAC. This released a DNA sequence fragment of 156 base pairs. The second aliquot was further digested with the restriction enzyme EcoRI which cleaves at the site of G AATTC. This released a DNA sequence fragment of 256 base pairs. The third aliquot was further digested with the restriction enzyme BstNI which cleaves at site CC TGG. This release a DNA sequence fragment of 433 base pairs. All of these fragments are now the 5' portion of the CAT gene. The 3' sequence end of the 256 and 433 bp fragments released by an EcoRI and a BstNI cleavage were end filled to generate blunt ends for ligation. The DNA was added to mix which included a mix of individual deoxynucleotides G, T, A and C and the Klenow fragment from DNA polymerase I. This adds the appropriate bases to the sequence to form a blunt double stranded sequence. A fourth construct was made by cleaving of the pBLCAT3 plasmid with the restriction enzyme EcoRI to remove a DNA sequence fragment 1407 bp in length. This fragment was further digested with the restriction enzyme DraI which cleaves at the site TTT AAA. This created a blunt ended fragment of 341 bp in length to span the 3' portion of the CAT gene sequence. Subsequent PvuII, Eco RI and BstNi digests released fragments of 154, 256 and 432 bp in length, respectively (FIG. 1). Referring to FIG. 1, fragments from the CAT gene clone, pBLCAT3, were fused to the RNA$^{met}_i$ gene located within a 650 bp soybean DNA fragment cloned into pSP72. Fragments P.24, B.9, and E.14 were cloned into the XhoI/HindIII site while D.15 was cloned into a unique PvuII site of PSP650-1. pCAMV/CAT/pA contains the full length CAT gene in the same orientation (8). A PstI digestion was used to reverse the orientation of the full length gene to form pCaMV/CC2. Arrows indicate the direction of transcription ($\rightarrow$) and direction of CAT coding sequence ($-\blacktriangle$).

A soybean (*Glycine max*) tRNA$^{met}_i$ gene contained on a 650 bp fragment was cloned into the Eco RI/HindIII restriction site of a pSP72 vector containing the SP6 and T7 RNA polymerase promoters (Promega Corp.) and yielding the pSP650-1 plasmid (22). The 2462 bp pSP72 vector was digested with the restriction enzyme EcoRI which cleaves at G AATTC and HindIII which cleaves at A AGCTT releasing a fragment of 51 bp and generating a 2411 bp vector with incompatible digested ends. The soybean genomic sequence was also digested with EcoRI and HindIII to release a 665 bp DNA fragment containing the tRNA methionine initiator gene with ends compatible to the now linearized pSP72 vector. The 665 bp fragment was ligated into the 2411 bp linearized pSP72 to create pSP650-1. These sequences include the coding region of the soybean tRNA$^{met}_i$ gene (72 bp in length), but not the RNA polymerase III termination signal and thereby permits readthrough into adjoining DNA. Plasmid pSP650-1 was digested at a unique HindIII site located in the 3' noncoding region and end-filled as described above to generate blunt ends. The end filled pSP650-1 plasmid was further digested at a unique XhoI site and the 154, 256 and 432 bp fragments were inserted to construct pGM/P.24, pGm/E.14 and pGm/B.9 respectively. The 341 bp DraI fragment was ligated into pSP650-1 at a unique PvuII site to yield plasmid pGm/D.15. The 780 bp CAT gene fragment was cloned in the sense direction into a plasmid containing the cauliflower mosaic virus 35S RNA promoter (CaMV) and the 250 bp nopaline synthase gene (NOS) poly A signal to form pCaMV/CAT/pA (8). The sense plasmid was digested with PstI and relegated in the reverse orientation to create an antisense CAT construct pCaMV/CC2.

Protoplast Isolation and Electroporation

Carrot suspension cell lines were grown in Murashige and Skoog (MS) medium containing 4 mg glycine, 2 mg NkA (a-napthaleneacetic acid) and 0.4 mg kinetin per liter. Cultures were grown on an orbital shaker at 160 rpm under low light intensity (less than 100 $\mu E/m^2/sec$) with 16/8 hours of day/night at 26° C. Cells were routinely subcultured at 7 days by a dilution of 1:4 in fresh medium. Protoplasts were prepared from rapidly growing cells four days post culture. Carrot cells were gently pelleted in a low speed centrifuge at 650 rpm at 4° C. for 5 minutes. A 7 to 8 ml packed volume was resuspended in 40 ml buffer containing 5 mM MES, 0.4M sorbitol and 2% driselase (Sigma Chemical Co.) at pH 5.0. This buffer was prepared beforehand, centrifuged at 5000 rpm for two hours, filter sterilized and stored at 20° C. for approximately three months without losing activity. The resuspended cells were gently agitated at 50 rpm for four hours at room temperature. Protoplasts were pelleted in a low speed centifuge at 425 rpm at 4° C. for five minutes and washed two times in electroporation buffer (10 mM Hepes, 150 mM NaCl, 5 mM CaCl$_2$ and 0.3M sorbitol at pH 7.1). Protoplasts were resuspended to a final volume of $3.6 \times 10^6$ cells/ml with 1 ml aliquots placed in 5 ml polyethylene vials. Sense and antisense plasmids were added to the protoplasts in a total volume of 100 $\mu$l and simultaneously electroporated. Stainless steel electrodes 1 cm apart were used with an electric pulse of 375 V/9.9 msec duration discharged by a 960 uF square wave capacitor. After a 10 minute incubation on ice, the 1 ml samples were added to 4 ml of MS medium (excluding hormones) to a final volume of $2.5 \times 10^5$ cells/ml in $15 \times 60$ mm sterile petri dishes. Incubation was in the dark at room temperature with no agitation. Viability was determined at various time points with the Evans Blue exclusion test.

Measurement of Gene Expression

Transient assays are now widely used as a tool to study gene expression by specific DNA sequences (25). Protoplasts were incubated for 24 hours, then pelleted at 400 rpm for five minutes at 4° C. The supernatant was removed and the protoplasts were transferred to 1.5 ml microcentrifuge tubes and centrifuged at 10,000 g for one minute at 4° C. The protoplasts were resuspended in 100 $\mu$l extraction buffer (2.5 mM EDTA, 250 mM Tris, 0.1% ascorbate and 1 mM phenylmethylsulphonylfluoride) and CAT assays were performed (26). Briefly, samples were sonicated and then incubated at 60° C. for 10 minutes to inactivate proteases, followed by centrifugation at 14,000 g for five minutes at room temperature. To 100 $\mu$l of supernatant, 5 $\mu$l of 10 mM acetyl coenzyme A (Sigma Chemical Co.) and 0.08 uCi of $^{14}$C-labeled chloramphenicol (47-60 mCi/mmol; New England Nuclear) were added and incubated at 37° C. for 30-60 minutes. The samples were extracted with 1 ml ethyl acetate, evaporated to dryness and resuspended in 10 $\mu$l ethyl acetate. These samples were spotted on silica gel thin layer plates and subjected to ascending chromatography with a 95:5 ratio of chloroform/methanol. Chloramphenicol and its acetylated forms were detected by autoradiography at room temperature for 12-48 hours and quantitated by scanning with a phosphorimager. A time course of CAT expression in carrot protoplasts was determined by sampling at various time points from 0-84 hours. Sample pellets were frozen in liquid nitrogen and stored at 70° C.

Results Of Experimentation

The application of the above procedures show the capacity of the antisense sequences transcribed by RNA polymerase III to inhibit foreign gene expression in plant cells. Constructs were made in which antisense sequences from portions of the bacterial CAT gene were fused to soybean tRNA$^{met}{}_i$ gene and these chimeric genes introduced into carrot protoplasts by electroporation. The antisense sequences were complementary to mRNAs transcribed by the RNA polymerase II using the CaMV 35S RNA promoter from DNAs simultaneously electroporated into carrot protoplasts.

To be able to examine a variety of antisense constructs, the transient assay system described above was developed so that it requires a small amount of target DNA. The optimum conditions for expression were then determined. In the above experiments, when only 1 μg of DNA encoding CAT driven by the CaMV 35 S RNA promoter was electroporated into carrot protoplasts, high levels of expression were observed as early as four hours and gradually increased to a peak at approximately 24 hours. This is in agreement with other reports where maximum expression of was observed between 4 to 24 hours when 2.5 μg (25) or 10 μg (32) of the CAT gene was introduced into tobacco protoplasts. In the present experiments, 1 μg of target DNA was used and protoplasts were harvested at 24 hours post electroporation. No carrier DNA was used except when necessary to compare nonspecific DNA effects.

Since the tRNA$^{met}{}_i$ gene is transcribed by RNA polymerase III, full length antisense CAT sequence RNAs would not be expected as termination occurs at sequences containing four or more thymidine residues (33). To confirm the expected transcripts, the antisense DNAs were transcribed with human 293 cell S100 nuclear extracts containing RNA polymerase III and requisite transcription factors and the products were analyzed on polyacrylamide gels (FIG. 2).

Figure 2:
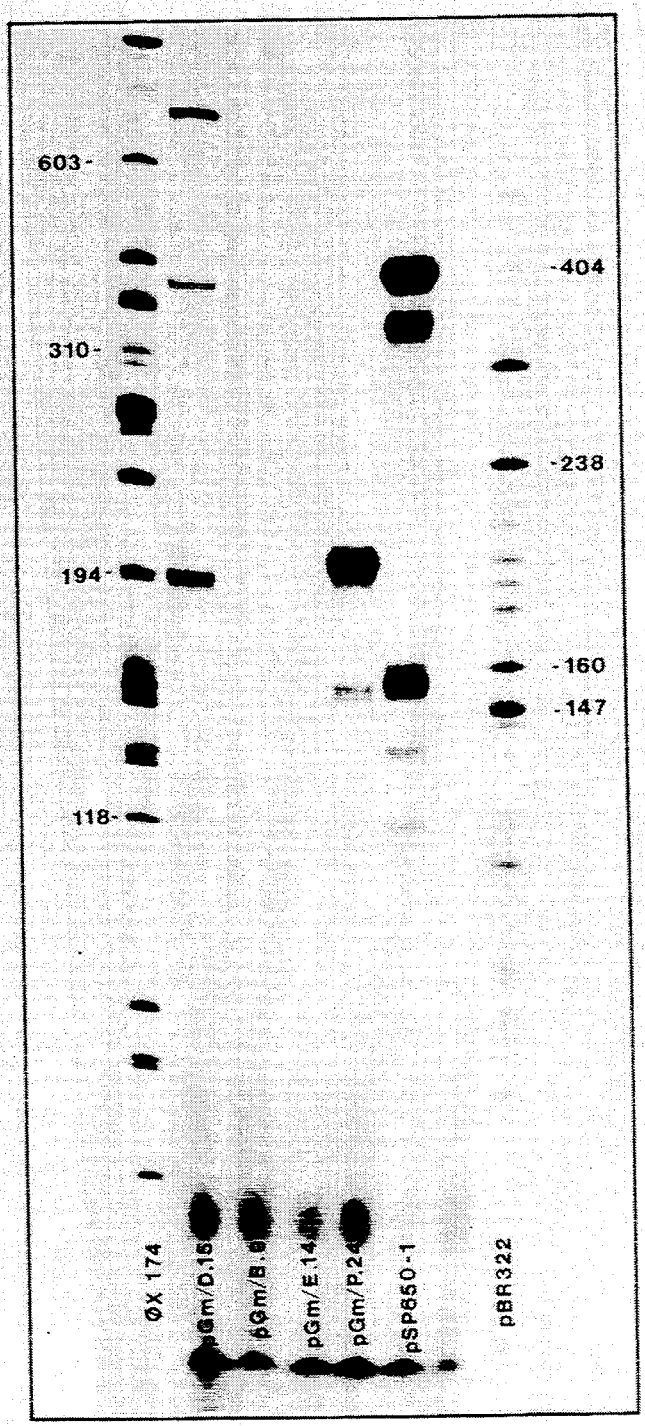
FIG. 2 shows in vitro transcription products.

More specifically referring to FIG. 2, pSP650-1, containing the soybean tRNA$^{met}{}_i$ gene and the tRNA$^{met}{}_i$ antisense constructs were assayed using a human 293 cell nuclear S100 extract and analyzed on 6% polyacrylamide gel. 500 ng of circular DNA was used for each reaction. φχ 174 HaeIII digest and pBR322 HpaII digest were used as markers. Construct pGm/P.24 yielded a major predicted product as approximately 200 bp with a minor band of about 150 bp. pGm/D.15 gave several transcripts of expected sizes with the most prominent being at approximately 200, 380 and 745 bp. Several minor transcripts also appeared. Surprisingly, two other constructs, pGm/E.14 and pGm/B.9, were not transcribed efficiently by this extract under these conditions. Since these assays were done in a heterologous in vitro system, it is not possible to predict to what extent these transcripts coincide with transcription in plant protoplasts.

Figure 3:
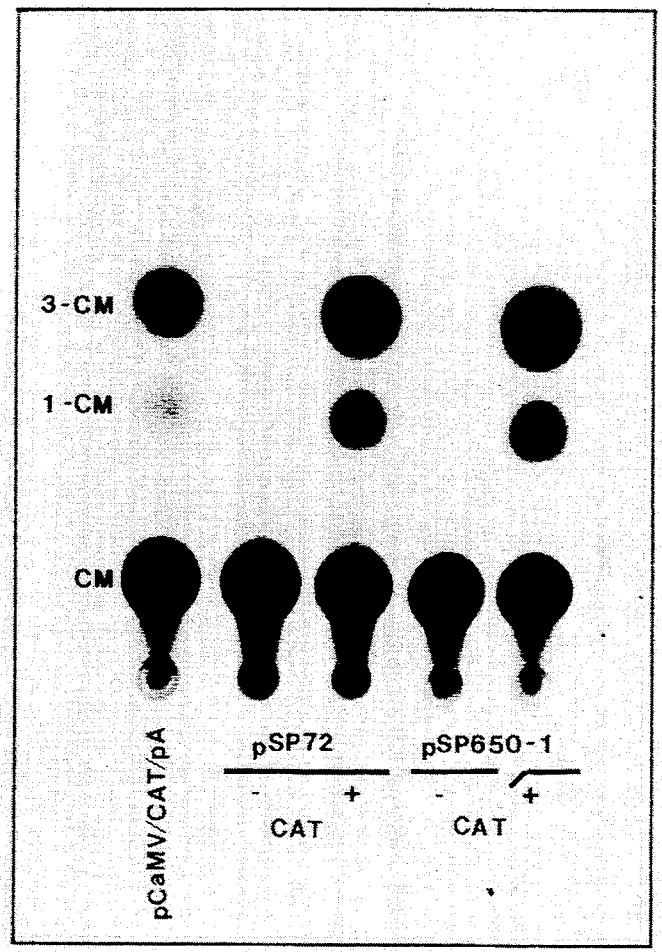
FIG. 3 shows effects of non-specific DNA on CAT activity.

Electroporation of the pSP72 vector DNA alone or pSP650-1, the DNA containing the soybean tRNA$^{met}{}_i$ without the linked CAT sequences, in carrot protoplasts, showed only a 2–3 fold increase in CAT gene expression (FIG. 3).

Figure 4:
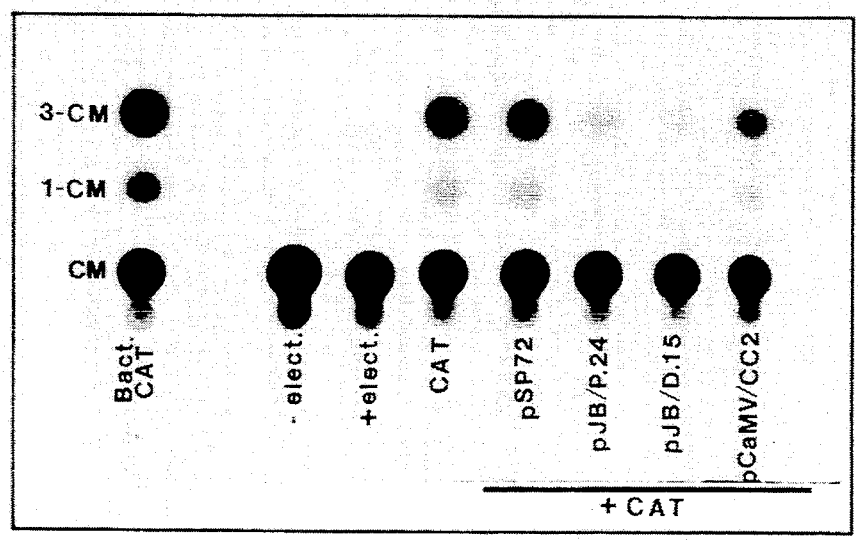
FIG. 4 shows a comparison of antisense clones driven by the soybean $tRNA^{met}_i$ gene and the CaMV 35S RNA promoter in suppressing CAT expression in transient assays.

The data indicate that the 3' cloned portion of the CAT gene fused to the soybean tRNA$^{met}{}_i$ gene is highly effective against suppressing CAT activity in electroporated carrot protoplasts. The antisense CAT construct of pGm/D.15 contains 184 bp of the 3' portion of the CAT coding region with 89 bp of trailer region plus 68 bp of non-specific vector DNA (FIG. 1). In six separate experiments, 100 μg of this antisense DNA construct, electroporated simultaneously with 1 μg of pCaMV/CAT/pA DNA, always suppressed CAT gene expression and, as shown in FIG. 4, up to as much as 90%. A reduction in expression of CAT was noted with sense:antisense ratios as low as 1:10 with this construct (data not shown). This is substantially greater than that seen with antisense CAT clones containing sequences complementary to the 5' region of CAT or with pCaMV/CC2, the full length antisense CAT gene driven by the CaMV 35S RNA promoter (FIG. 4). More specifically referring to FIG. 4, 1 μg of CAT sense DNA was electroporated alone or simultaneously with 100 μg of antisense or non-specific DNA into carrot protoplasts. In FIG. 4, Bact. CAT=bacterial CAT extract; −elec.=control protoplasts not electroporated; +elect.=control protoplasts electroporated without the addition of DNA; pCaMV-/CAT/pA=sense CAT; pSP72 (non-specific DNA)=-vector containing the SP6 and T7 promoters; pGM/P.24 and pGm/D.15=5' and 3' antisense CAT constructs, respectively, behind the tRNA$^{met}{}_i$ gene; pCaMV/CC2=full length antisense CAT gene driven by the CaMV 35S RNA promoter; CM—chloramphenicol; 1-CM—chloramphenicol 1-acetate; 3-CM=chloramphenicol 3-acetate.

Figure 5:
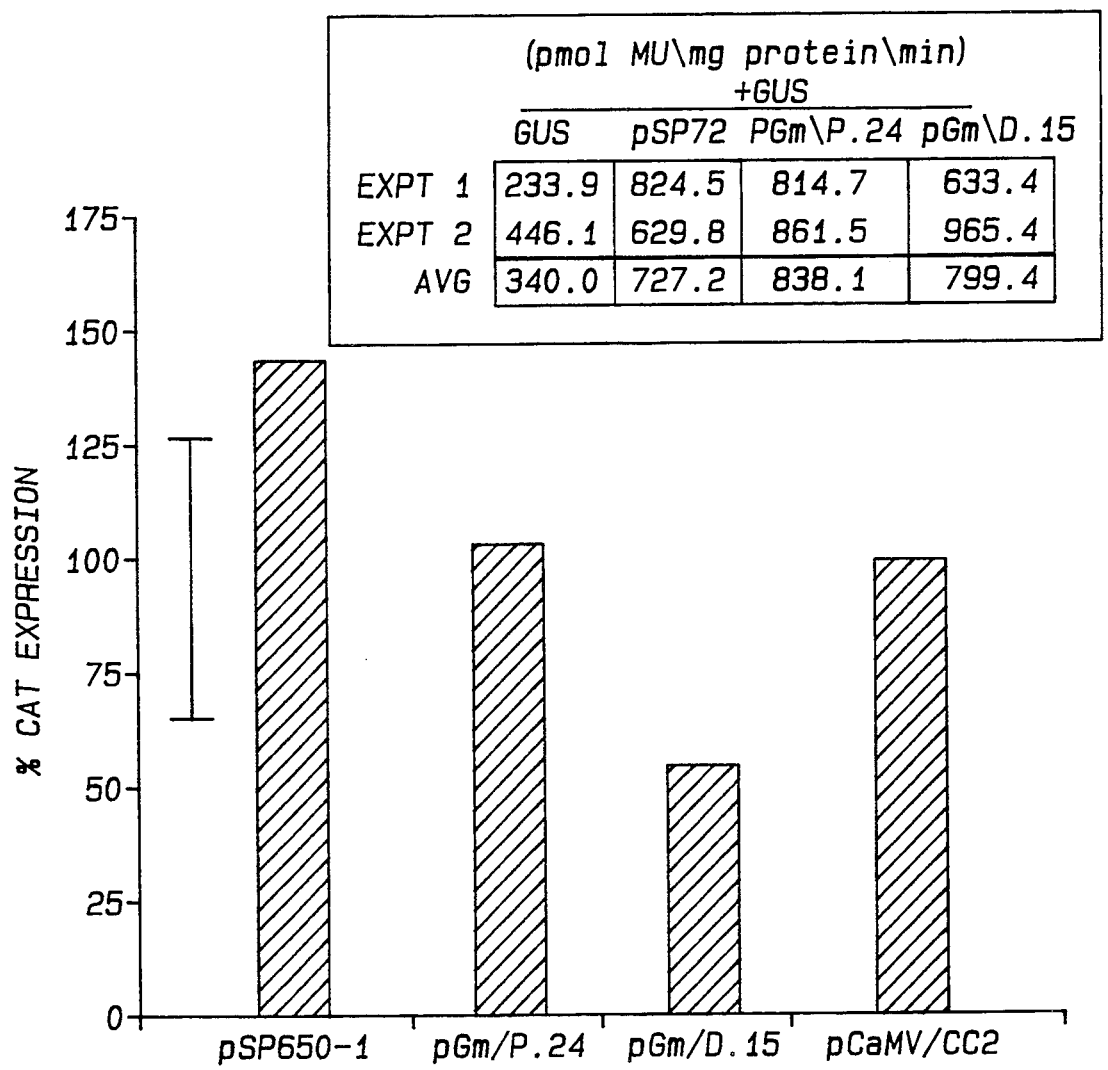
FIG. 5 shows the quantitative analysis on the level of CAT gene expression by antisense constructs from various experiments.

The clone pGm/P.24 contains 114 bp of antisense DNA complementary to the 5' CAT coding region plus 29 bases of leader sequences (from the bacterial Tn9 transposon) and 9 bases of a synthetic polylinker region (FIG. 1). It also suppresses CAT gene expression, but at a somewhat reduced level compared to pGm/D.15 (FIGS. 4,5).

The 5' complementary CAT sequence transcribed by the tRNA$^{met}{}_i$ was found to be more effective at suppressing CAT activity than the full length antisense driven by the CaMV 35S RNA promoter (FIG. 5), indicating that the 5' region can be engineered to be an effective antisense template. Two longer 5' antisense clones, pGm/E.14 and pGm/B.9, with 214 and 391 bp respectively of sequence complementary to CAT and DNA, demonstrated little suppression of CAT activity (data not shown). However, these two clones were not transcribed efficiently in the in vitro extracts (FIG. 2) which may account for their minimal effects on target DNA.

To demonstrate that the tRNA/CAT fusion constructs specifically suppressed the CAT gene, we included another marker gene, the beta-glucuronidase (GUS) gene (42), in our electroporation experiments. Neither the vector (a non-specific plasmid) nor the antisense constructs suppressed GUS activity (Table 1).

TABLE 1

|  | GUS | (pmol MU/mg protein/min) +GUS | | |
|---|---|---|---|---|
|  |  | pSP72 | pGm/P.24 | pGm/D.15 |
| EXPT 1 | 233.9 | 824.5 | 814.7 | 633.4 |
| EXPT 2 | 446.1 | 629.8 | 861.5 | 965.4 |
| AVG | 340.0 | 727.2 | 838.1 | 799.4 |

Table 1 shows specificity of antisense CAT constructs for the target CAT gene. But instead, these constructs, enhanced the level of GUS expression when compared to enzyme activity where the GUS DNA was electroporated alone. Such an effect on GUS activity has been noted previously in carrot protoplasts where carrier DNA was electroporated with GUS RNA.

The specific suppression of CAT activity caused by the 3' CAT/tRNA fusion construct, pGM/D.15, varied from experiment to experiment, but it was always the most effective of the constructs employed. The 5' antisense CAT sequence transcribed by the tRNA$^{me\text{-}}$$_{ti}$pGm/P.24, was at least as effective at suppressing CAT activity as the full length antisense CAT gene driven by the CaMV 35S RNA promoter (FIG. 5). With sense to antisense ratios ranging from 1:1 to 1:500, with or without the addition of carriers to enhance the sense message, or with mixing to sustain comparable DNA levels, the greatest level of suppression we observed with pCaMV/CC2 was less than a three-fold reduction of basal level expression (FIG. 5). This suggests that suppression of CAT activity with antisense sequences driven by the tRNA$^{met}$$_i$ promoter may be more efficient than with the CaMV 35S RNA promoter, although it is difficult to make a direct comparison because of the differences in antisense transcript size caused by transcription termination and processing.

It can be concluded from the above results that antisense RNA templates transcribed by RNA polymerase III can efficiently suppress gene expression in plant cells and perhaps to a greater extent than the CaMV 35S RNA promoter.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES

1. Sherwood, J. L. & Fulton, R. W. (1982) *Virology* 119, 150–158.
2. Houba-Hérin, N. & Inouye, M. (1987) in *Nucleic Acids and Molecular Biology* eds. Eckstein, F. & Lilley, D. M. J. (Springer-Verlag, Berlin) Vol. 1, pp. 210–220.
3. Kim, S. K. & Wold, B. J. (1985) *Cell* 42, 129–138.
4. Melton, D. A. (1985) *Proc. Natl. Acad. Sci. USA* 82, 144–148.
5. Green, P. J., Pines, O., & Inouye, M. (1986) *Ann. Rev. Biochem.* 55, 567–597.
6. van der Krol, A. R., Lenting, P. E., Veenstra, J., van der Meer, I. E., Koes, R. E., Gerats, A. G. M., Mol, J. N. M. & Stuitje, A. R. (1988) *Nature* (London) 333, 866–869.
7. Abel, P. P., Stark, D. M., Sanders, P. R., & Beachy, R. N. (1989) *Proc. Natl. Acad. Sci. USA* 86, 6949–6952.
8. Ecker, J. R. & Davis, R. W. (1986) *Proc. Natl. Acad. Sci. USA* 83, 5372–5376.
9. Hemenway, C., Fang, R. X., Kaniewski, W. K., Chua, N. H. & Tumer, T. E. (1988) *EMBO J.* 7, 1273–1280.
10. Rodermel, S. R., Abbott, M. S. & Bogorad, L. (1988) *Cell* 55, 673–681.
11. Rothstein, S. J., DiMaio, J., Strand, M. & Rice, D. (1987) *Proc. Natl. Acad. Sci.* 84, 8439–8443.
12. Cuozzo, M., O,Connell, K. M., Kaniewski, W., Fang, R. X., Chua, N. H. & Turner, N. E. (1988) *Bio/Technology* 6, 549–557.
13. Smith, C. J. S., Watson, C. F., Ray, J., Bird, C. R., Morris, P. C., Schuch, W. & Grierson, D. (1988) *Nature* (London) 334, 724–726.
14. Hamilton, A. J., Lycett, G. W. & Grierson, D. (1990) *Nature* (London) 346, 284–287.
15. Stockhaus, J., Hofer, M., Renger, G., Westhoff, P., Wydrzynski, T. & Willmitzer, L. (1990) *EMBO J.* 9, 3013–3021.
16. Takayama, K. M. & Inouye, M. (1990) *CRC Crit. Rev. Biochem. & Mol. Biol.* 25, 155–184.
17. Sharp, S. J., Schaack, J., Cooley, L., Burke, D. J. & Soll, D. (1985) *CRC Crit. Rev. in Biochem.* 19, 107–144.
18. Santos, T. & Zasloff, M. (1981) *Cell* 23, 699–709.
19. Jennings, P. A. & Molloy, P. L. (1987) *EMBO J.* 6, 3043–3047.
20. Sullenger, B. A., Lee, T. C., Smith, C. A., Ungers, G. E. & Gilboa, E. (1990) *Mol. Cell. Biol.* 10, 6512–6523.
21. Sullenger, B. A., Gallardo, H. F., Ungers, G. E. & Gilboa, E. (1990) *Cell* 63, 601–608.
22. Inouye, M. (1988) *Gene* 72, 25–34.
23. Rebagliati, M. R. & Melton, M. A. (1987) *Cell* 48, 599–605.
24. Bass, B. L. & Weintraub, H. (1987) *Cell* 48, 607–613.
25. Chang, L. J. & Stoltzfus, C. M. (1985) *Mol. Cell. Biol.* 5, 2341–2348.
26. van der Krol, A. R. M., Mol, J. N. M. & Stuitje, A. R. (1988) *Gene* 72, 45–50.
27. Smith, C. C., Aurelian, L., Reddy, M., Miller, P. S. & Ts'O, P. O. P. (1986) *Proc. Natl. Acad. Sci. USA* 83, 2787–2791.
28. Zamecnik, P. C., Goodchild, J., Taguchi, Y. & Sarin, P. S. (1986) *Proc. Natl. Acad. Sci. USA* 83, 4143–4146.
29. Sandler, S. J., Stayton, M., Townsend, J. A., Ralston, N. L., Bedbrook, J. R. & Dunsmuir, P. (1988) *Plant Mol. Biol.* 11, 301–310.
30. Töpfer, R., Pröls, M. Schell, J. & Steinbiss, H. H. (1988) *Plant Cell Rep.* 7, 225–228.
31. Takamatsu, N., Ishikawa, M., Meshi, T. & Okada, Y. (1987) *EMBO J.* 6, 307–311.
32. Ebert, P. R., Ha, S. B. & An, G. (1978) *Proc. Natl. Acad. Sci. USA* 84, 5745–5749.
33. Pröls, M., Töpfer, R., Schell, J. & Steinbiss, H. H. (1988) *Plant Cell Rep.* 7, 221–224.
34. Bogenhagen, D. F. & Brown, D. D. (1981) *Cell* 24, 261–270.
35. Inouye, M. (1988) *Gene* 72, 25–34.
36. Chang, L. J. & Stoltzfus, C. M. (1985) *Mol. Cell Biol.* 5, 2341–2348.
37. van der Krol, A. R. M., Mol, J. N. M. & Stuitje, A. R. (1988) *Gene* 72, 45–50.
38. Smith, C. C., Aurelian, L., Reddy, M. Miller, P. S. & Ts'O, P. O. P. (1986) *Proc. Natl. Acad. Sci. USA* 83, 2787–2791.
39. Zamecnik, P. C., Goodchild, J., Taguchi, Y. & Sarin, P. S. (1986) *Proc. Natl. Acad. Sci. USA* 83, 4143–4146.
40. Sandler, S. J., Stayton, M., Townsend, J. A., Ralston, N. L., Bedbrook, J. R. & Dunsmuir, P. (1988) *Plant Mol. Biol.* 11, 301–310.
41. Benfey, P. N., Ren, L., & Chua, N. H. (1990) *EMBO J.* 9, 1677–1684.
42. Benfey, P. N., Ren, L., & Chua, N. H. (1990) *EMBO J.* 9, 1685–1696.
43. Jefferson, R. A., Kavanaugh, T. A. & Bevan, M. W. (1987) *EMBO J.* 6, 3043–3047.

44. Mascarenhas, J. P. (1991) *J. Cell Biochem.* 15A, 32 (abstr.)

45. van der Krol, A. R., Stuitje, A. R. & Mol, J. N. M. (1991) in *Antisense Nucleic Acids and Proteins* eds. Mol, J. N. M. & van der Krol, A. R. (Marcel Dekker, New York), pp. 125–141.

What is claimed is:

1. An expression system for use in plants to suppress foreign gene expression, said system consisting essentially of: a constitutive promoter element from a plant tRNA methionine initiator (tRNA$^{met}$) gene, said promoter element lacking a terminator, and a DNA sequence in reverse orientation fused to said promoter element for being co-transcribed with said promoter element by an RNA polymerase III to inhibit expression of the foreign gene.

2. A system as set forth in claim 1 wherein said tRNA$^{met}_i$ gene is derived from soybean said gene consisting essentially of 72 bp of coding sequence.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( v i ) ORIGINAL SOURCE:
        ( A ) ORGANISM: Glycine max ( i x ) FEATURE:
        ( A ) NAME/KEY: primtranscript
        ( B ) LOCATION: 172..243

( x i ) SEQUENCE DESCRIPTION: SEQ ID NO:1:

```
TCGAGGAGCT  TGGCGAGATT  TTCAGGAGCT  AAGGAAGCTA  AAATGGAGAA  AAAAATCACT      60
GGATATACCA  CCGTTGATAT  ATCCAATGG   CATCGTAAAG  AACATTTGA   GGCATTTCAG     120
TCAGTTGCTC  AATGTACCTA  TAACCAGACC  GTTCAGAGCT  TTTCTCTTTT  ATATCAGAGC    180
CAGGTTTCGA  TCCTGGGACC  TGTGGGTTAT  GGGCCCACCA  CGCTTCCGCT  GCGCCACTCT    240
GATTTAATGG  TTTTTACTTT  TGGCAAGCTA  TGTATTTATT  TATTTTTGA   AATGTGTTAT    300
TTTGTAAGTT  TGGGAGGGC   ACAGTAGTAG  AGAATGGTTA  TAAGGTGATT  TGGATGCTTC    360
CTCTTACGTG  TCAAGACAGT  CAAGTGAGCG  TAT                                   393
```

( 2 ) INFORMATION FOR SEQ ID NO:2:

( i ) SEQUENCE CHARACTERISTICS:
        ( A ) LENGTH: 497 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( v i ) ORIGINAL SOURCE:
        ( A ) ORGANISM: Glycine max ( i x ) FEATURE:
        ( A ) NAME/KEY: primtranscript
        ( B ) LOCATION: 275..347

( i x ) FEATURE:
        ( A ) NAME/KEY: primtranscript
        ( B ) LOCATION: 276..347

( x i ) SEQUENCE DESCRIPTION: SEQ ID NO:2:

```
TCGAGGAGCT  TGGCGAGATT  TTCAGGAGCT  AAGGAAGCTA  AAATGGAGAA  AAAAATCACT      60
GGATATACCA  CCGTTGATAT  ATCCAATGG   CATCGTAAAG  AACATTTGA   GGCATTTCAG     120
TCAGTTGCTC  AATGTACCTA  TAACCAGACC  GTTCAGCTGG  ATATTACGGC  CTTTTTAAAG    180
ACCGTAAAGA  AAAATAAGCA  CAAGTTTTAT  CCGGCCTTTA  TTCACATTCT  TGCCCGCCTG    240
```

-continued

| ATGAATGCTC | ATCCGGAATT | AGCTTTCTC | TTTTATATCA | GAGCCAGGTT | TCGATCCTGG | 300 |
| GACCTGTGGG | TTATGGGCCC | ACCACGCTTC | CGCTGCGCCA | CTCTGATTTA | ATGGTTTTA | 360 |
| CTTTTGGCAA | GCTATGTATT | TATTTATTTT | TTGAAATGTG | TTATTTGTA | AGTTTTGGGA | 420 |
| GGGCACAGTA | GTAGAGAATG | GTTATAAGGT | GATTTGGATG | CTTCCTCTTA | CGTGTCAAGA | 480 |
| CAGTCAAGTG | AGCGTAT | | | | | 497 |

(2) INFORMATION FOR SEQ ID NO:3:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (A) ORGANISM: Glycine max (ix) FEATURE:
        (A) NAME/KEY: primtranscript
        (B) LOCATION: 451..522

(xi) SEQUENCE DESCRIPTION: SEQ ID NO:3:

| TCGAGGAGCT | TGGCGAGATT | TTCAGGAGCT | AAGGAAGCTA | AAATGGAGAA | AAAAATCACT | 60 |
| GGATATACCA | CCGTTGATAT | ATCCCAATGG | CATCGTAAAG | AACATTTTGA | GGCATTTCAG | 120 |
| TCAGTTGCTC | AATGTACCTA | TAACCAGACC | GTTCAGCTGG | ATATTACGGC | CTTTTAAAG | 180 |
| ACCGTAAAGA | AAAATAAGCA | CAAGTTTTAT | CCGGCCTTTA | TTCACATTCT | TGCCCGCCTG | 240 |
| ATGAATGCTC | ATCCGGAATT | CCCGTATGGC | AATGAAAGAC | GGTGAGCTGG | TGATATGGGA | 300 |
| TAGTGTTCAC | CCTTGTTACA | CCGTTTTCCA | TGAGCAAACT | GAAACGTTTT | CATCGCTCTG | 360 |
| GAGTGAATAC | CACGACGATT | TCCGGCAGTT | TCTACACATA | TATTCGCAAG | ATGTGGCGTG | 420 |
| TTACGGTGAA | AACCTAGCTT | TTCTCTTTTA | TATCAGAGCC | AGGTTTCGAT | CCTGGGACCT | 480 |
| GTGGGTTATG | GGCCCACCAC | GCTTCCGCTG | CGCCACTCTG | ATTAATGGT | TTTTACTTTT | 540 |
| GGCAAGCTAT | GTATTTATTT | ATTTTTTGAA | ATGTGTTATT | TTGTAAGTTT | TGGGAGGGCA | 600 |
| CAGTAGTAGA | GAATGGTTAT | AAGGTGATTT | GGATGCTTCC | TCTTACGTGT | CAAGACAGTC | 660 |
| AAGTGAGCGT | AT | | | | | 672 |

(2) INFORMATION FOR SEQ ID NO:4:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
        (A) ORGANISM: Glycine max (ix) FEATURE:
        (A) NAME/KEY: primtranscript
        (B) LOCATION: 360..431

(xi) SEQUENCE DESCRIPTION: SEQ ID NO:4:

| AGCTAAACGT | GGCCAATATG | GACAACTTCT | TCGCCCCCGT | TTTCACCATG | GGCAAATATT | 60 |
| ATACGCAAGG | CGACAAGGTG | CTGATGCCGC | TGGCGATTCA | GGTTCATCAT | GCCGTCTGTG | 120 |

-continued

| | | | | | | |
|---|---|---|---|---|---|---|
| ATGGCTTCCA | TGTCGGCAGA | ATGCTTAATG | AATTACAACA | GTACTGCGAT | GAGTGGCAGG | 180 |
| GCGGGGCGTA | ATTTTTTTAA | GGCAGTTATT | GGTGCCCTTA | AACGCCTGGT | GCTACGCCTG | 240 |
| AATAAGTGAT | AATAAGCGGA | TGAATGGCAG | AAATTCGCCG | GATCTTTGTG | AAGGAACCTT | 300 |
| ACTTCTGTGG | TGTGACATAA | TTGGACAAAC | TACCTACAGA | GTTTAGCTTT | TCTCTTTTAT | 360 |
| ATCAGAGCCA | GGTTTCGATC | CTGGGACCTG | TGGGTTATGG | GCCCACCACG | CTTCCGCTGC | 420 |
| GCCACTCTGA | TTTAATGGTT | TTTACTTTTG | GCAAGCTATG | TATTTATTTA | TTTTTTGAAA | 480 |
| TGTGTTATTT | TGTAAGTTTT | GGGAGGGCAC | AGTAGTAGAG | AATGGTTATA | AGGTGATTTG | 540 |
| GATGCTTCCT | CTTACGTGTC | AAGACAGTCA | AGTGAGCGTA | T | | 581 |